US008482415B2

(12) United States Patent
Sanchez et al.

(10) Patent No.: US 8,482,415 B2
(45) Date of Patent: Jul. 9, 2013

(54) INTERACTIVE MULTILEVEL ALARM

(75) Inventors: Gabriel Sanchez, Valley Center, CA (US); Nirav Patel, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 417 days.

(21) Appl. No.: 12/760,709

(22) Filed: Apr. 15, 2010

(65) Prior Publication Data
US 2011/0133936 A1 Jun. 9, 2011

Related U.S. Application Data

(60) Provisional application No. 61/266,692, filed on Dec. 4, 2009.

(51) Int. Cl.
G08B 23/00 (2006.01)
G08B 5/00 (2006.01)
G08B 5/22 (2006.01)
G08B 1/08 (2006.01)
A61M 15/00 (2006.01)

(52) U.S. Cl.
USPC ............... 340/573.1; 340/815.4; 340/815.45; 340/286.07; 340/539.12; 128/200.24

(58) Field of Classification Search
USPC ............. 340/573.1, 815.4, 815.45, 286.07, 340/815.48, 539.12; 128/200.24–207.29; 345/156, 173
See application file for complete search history.

(56) References Cited

U.S. PATENT DOCUMENTS

| | | | |
|---|---|---|---|
| 4,752,089 A | 6/1988 | Carter | |
| 4,838,259 A * | 6/1989 | Gluck et al. | 128/204.21 |
| 4,921,642 A | 5/1990 | LaTorraca | |
| 4,954,799 A | 9/1990 | Kumar | |
| 5,057,822 A | 10/1991 | Hoffman | |
| 5,072,737 A | 12/1991 | Goulding | |
| 5,107,831 A | 4/1992 | Halpern et al. | |
| 5,150,291 A | 9/1992 | Cummings et al. | |
| 5,158,534 A | 10/1992 | Berry et al. | |

(Continued)

FOREIGN PATENT DOCUMENTS

| | | |
|---|---|---|
| WO | 9841267 A1 | 9/1998 |
| WO | WO 9947200 | 9/1999 |

(Continued)

OTHER PUBLICATIONS

PCT International Search Report, Date of mailing Apr. 6, 2011, International application No. PCT/US2010/058854, International filing date Dec. 3, 2010, Applicant Nellcor Puritan Bennett LLC.

(Continued)

*Primary Examiner* — Brian Zimmerman
*Assistant Examiner* — Laura Nguyen

(57) ABSTRACT

This disclosure describes embodiments of alarm systems and methods for use in devices such as medical ventilators. Embodiments described below provide for an apparatus of an interactive multilevel alarm system. Embodiments of the alarms also provide, at a glance, current alarm and device status information and historical alarm information to the operator. Embodiments also direct interaction with the alarming functions of the device by the operator. In some embodiments, additional visual indicators may be provided to identify non-normal or noteworthy operating conditions, such as the use of a therapeutic gas by a mechanical ventilator, so that the operator can assess the impact of that non-normal condition on any current and historical alarm information simultaneously provided.

20 Claims, 11 Drawing Sheets
(5 of 11 Drawing Sheet(s) Filed in Color)

U.S. PATENT DOCUMENTS

| | | | |
|---|---|---|---|
| 5,161,525 A | 11/1992 | Kimm et al. | |
| 5,237,987 A | 8/1993 | Anderson et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,319,540 A | 6/1994 | Isaza et al. | |
| 5,325,861 A | 7/1994 | Goulding | |
| 5,333,606 A | 8/1994 | Schneider et al. | |
| 5,339,807 A | 8/1994 | Carter | |
| 5,343,857 A | 9/1994 | Schneider et al. | |
| 5,351,522 A | 10/1994 | Lura | |
| 5,355,893 A | 10/1994 | Mick et al. | |
| 5,357,946 A | 10/1994 | Kee et al. | |
| 5,368,019 A | 11/1994 | LaTorraca | |
| 5,383,449 A | 1/1995 | Forare et al. | |
| 5,385,142 A | 1/1995 | Brady et al. | |
| 5,390,666 A | 2/1995 | Kimm et al. | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,513,631 A | 5/1996 | McWilliams | |
| 5,517,983 A | 5/1996 | Deighan et al. | |
| 5,520,071 A | 5/1996 | Jones | |
| 5,520,192 A | 5/1996 | Kitney et al. | |
| 5,524,615 A | 6/1996 | Power | |
| 5,531,221 A | 7/1996 | Power | |
| 5,534,851 A | 7/1996 | Russek | |
| 5,542,415 A | 8/1996 | Brady | |
| 5,544,674 A | 8/1996 | Kelly | |
| 5,549,106 A | 8/1996 | Gruenke et al. | |
| 5,590,648 A | 1/1997 | Mitchell et al. | |
| 5,596,984 A | 1/1997 | O'Mahoney et al. | |
| 5,598,838 A | 2/1997 | Servidio et al. | |
| 5,611,335 A | 3/1997 | Makhoul et al. | |
| 5,630,411 A | 5/1997 | Holscher | |
| 5,632,270 A | 5/1997 | O'Mahoney et al. | |
| 5,640,149 A | 6/1997 | Campbell | |
| 5,645,048 A | 7/1997 | Brodsky et al. | |
| 5,660,171 A | 8/1997 | Kimm et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,678,539 A | 10/1997 | Schubert et al. | |
| 5,687,717 A | 11/1997 | Halpern et al. | |
| 5,715,812 A | 2/1998 | Deighan et al. | |
| 5,752,506 A | 5/1998 | Richardson | |
| 5,762,480 A | 6/1998 | Adahan | |
| 5,771,884 A | 6/1998 | Yarnall et al. | |
| 5,791,339 A | 8/1998 | Winter | |
| 5,794,986 A | 8/1998 | Gansel et al. | |
| 5,813,399 A | 9/1998 | Isaza et al. | |
| 5,819,723 A | 10/1998 | Joseph | |
| 5,826,575 A | 10/1998 | Lall | |
| 5,829,441 A | 11/1998 | Kidd et al. | |
| 5,864,938 A | 2/1999 | Gansel et al. | |
| 5,865,168 A | 2/1999 | Isaza | |
| 5,881,717 A | 3/1999 | Isaza | |
| 5,881,723 A | 3/1999 | Wallace et al. | |
| 5,884,623 A | 3/1999 | Winter | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,931,160 A | 8/1999 | Gilmore et al. | |
| 5,934,274 A | 8/1999 | Merrick et al. | |
| 5,956,023 A | 9/1999 | Lyle et al. | |
| 5,966,760 A | 10/1999 | Gallant et al. | |
| 6,024,089 A * | 2/2000 | Wallace et al. | 128/204.21 |
| 6,041,780 A | 3/2000 | Richard et al. | |
| 6,047,860 A | 4/2000 | Sanders | |
| 6,076,523 A | 6/2000 | Jones et al. | |
| 6,116,240 A | 9/2000 | Merrick et al. | |
| 6,116,464 A | 9/2000 | Sanders | |
| 6,123,073 A | 9/2000 | Schlawin et al. | |
| 6,135,106 A | 10/2000 | Dirks et al. | |
| 6,142,150 A | 11/2000 | O'Mahony et al. | |
| 6,161,539 A | 12/2000 | Winter | |
| 6,203,502 B1 | 3/2001 | Hilgendorf et al. | |
| 6,220,245 B1 | 4/2001 | Takabayashi et al. | |
| 6,269,812 B1 | 8/2001 | Wallace et al. | |
| 6,273,444 B1 | 8/2001 | Power | |
| 6,283,119 B1 | 9/2001 | Bourdon | |
| 6,305,373 B1 | 10/2001 | Wallace et al. | |
| 6,321,748 B1 | 11/2001 | O'Mahoney | |
| 6,325,785 B1 | 12/2001 | Babkes et al. | |
| 6,357,438 B1 | 3/2002 | Hansen | |
| 6,360,745 B1 | 3/2002 | Wallace et al. | |
| 6,369,838 B1 | 4/2002 | Wallace | |
| 6,390,091 B1 | 5/2002 | Banner et al. | |
| 6,406,426 B1 | 6/2002 | Reuss et al. | |
| 6,412,483 B1 | 7/2002 | Jones et al. | |
| 6,439,229 B1 | 8/2002 | Du et al. | |
| 6,467,478 B1 | 10/2002 | Merrick et al. | |
| 6,546,930 B1 | 4/2003 | Emerson et al. | |
| 6,553,991 B1 | 4/2003 | Isaza | |
| 6,557,553 B1 | 5/2003 | Borrello | |
| 6,571,795 B2 | 6/2003 | Bourdon | |
| 6,575,902 B1 | 6/2003 | Burton | |
| 6,579,232 B2 | 6/2003 | Sakamaki et al. | |
| 6,622,726 B1 | 9/2003 | Du | |
| 6,644,310 B1 | 11/2003 | Delache et al. | |
| 6,668,824 B1 | 12/2003 | Isaza et al. | |
| 6,675,801 B2 | 1/2004 | Wallace et al. | |
| 6,718,974 B1 | 4/2004 | Moberg | |
| 6,725,447 B1 | 4/2004 | Gilman et al. | |
| 6,739,337 B2 | 5/2004 | Isaza | |
| 6,761,167 B1 | 7/2004 | Nadjafizadeh et al. | |
| 6,761,168 B1 | 7/2004 | Nadjafizadeh et al. | |
| 6,796,305 B1 | 9/2004 | Banner et al. | |
| 6,814,074 B1 | 11/2004 | Nadjafizadeh et al. | |
| 6,866,040 B1 | 3/2005 | Bourdon | |
| 6,876,303 B2 | 4/2005 | Reeder et al. | |
| 6,956,572 B2 | 10/2005 | Zaleski | |
| 6,960,854 B2 | 11/2005 | Nadjafizadeh et al. | |
| 7,036,504 B2 | 5/2006 | Wallace et al. | |
| 7,044,930 B2 | 5/2006 | Strömberg | |
| 7,077,131 B2 | 7/2006 | Hansen | |
| RE39,225 E | 8/2006 | Isaza et al. | |
| 7,117,438 B2 | 10/2006 | Wallace et al. | |
| 7,162,296 B2 | 1/2007 | Leonhardt et al. | |
| 7,210,478 B2 | 5/2007 | Banner et al. | |
| 7,237,205 B2 | 6/2007 | Sarel | |
| 7,263,995 B2 | 9/2007 | Gurneé et al. | |
| 7,270,126 B2 | 9/2007 | Wallace et al. | |
| 7,290,544 B1 | 11/2007 | Säreläet al. | |
| 7,320,321 B2 | 1/2008 | Pranger et al. | |
| 7,327,219 B2 | 2/2008 | Lederer, IV | |
| 7,343,917 B2 | 3/2008 | Jones | |
| 7,369,757 B2 | 5/2008 | Farbarik | |
| 7,370,650 B2 | 5/2008 | Nadjafizadeh et al. | |
| 7,428,902 B2 | 9/2008 | Du et al. | |
| 7,460,959 B2 | 12/2008 | Jafari | |
| 7,487,773 B2 | 2/2009 | Li | |
| 7,654,802 B2 | 2/2010 | Crawford, Jr. et al. | |
| 7,694,677 B2 | 4/2010 | Tang | |
| 7,717,113 B2 | 5/2010 | Andrieux | |
| 7,721,736 B2 | 5/2010 | Urias et al. | |
| D618,356 S | 6/2010 | Ross | |
| 7,784,461 B2 | 8/2010 | Figueiredo et al. | |
| 7,823,588 B2 | 11/2010 | Hansen | |
| 7,855,716 B2 | 12/2010 | McCreary et al. | |
| D632,796 S | 2/2011 | Ross et al. | |
| D632,797 S | 2/2011 | Ross et al. | |
| 7,891,354 B2 | 2/2011 | Farbarik | |
| 7,893,560 B2 | 2/2011 | Carter | |
| D638,852 S | 5/2011 | Skidmore et al. | |
| 7,984,714 B2 | 7/2011 | Hausmann et al. | |
| D643,535 S | 8/2011 | Ross et al. | |
| 7,992,557 B2 | 8/2011 | Nadjafizadeh et al. | |

| | | |
|---|---|---|
| 8,001,967 B2 | 8/2011 | Wallace et al. |
| 8,021,310 B2 | 9/2011 | Sanborn et al. |
| D649,157 S | 11/2011 | Skidmore et al. |
| 8,113,062 B2 | 2/2012 | Graboi et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0026941 A1 | 3/2002 | Biondi et al. |
| 2003/0156143 A1 | 8/2003 | Westenskow et al. |
| 2003/0189492 A1 | 10/2003 | Harvie |
| 2004/0133123 A1 | 7/2004 | Leonhardt et al. |
| 2004/0221845 A1 | 11/2004 | Pranger et al. |
| 2005/0033124 A1 | 2/2005 | Kelly et al. |
| 2005/0039748 A1 | 2/2005 | Andrieux |
| 2005/0061321 A1 | 3/2005 | Jones |
| 2005/0098178 A1 | 5/2005 | Banner et al. |
| 2005/0112325 A1 | 5/2005 | Hickle |
| 2005/0139212 A1 | 6/2005 | Bourdon |
| 2005/0172966 A1 | 8/2005 | Blaise et al. |
| 2007/0000494 A1 | 1/2007 | Banner et al. |
| 2007/0017515 A1 | 1/2007 | Wallace et al. |
| 2007/0068523 A1 | 3/2007 | Fishman |
| 2007/0077200 A1 | 4/2007 | Baker |
| 2007/0227537 A1 | 10/2007 | Bemister et al. |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097143 A1 | 4/2008 | Califorrniaa |
| 2008/0097234 A1 | 4/2008 | Nicolazzi et al. |
| 2008/0183054 A1 | 7/2008 | Kroeger et al. |
| 2009/0054743 A1 | 2/2009 | Stewart |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132371 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |

FOREIGN PATENT DOCUMENTS

| | | |
|---|---|---|
| WO | 2006074251 A2 | 7/2006 |
| WO | WO2007145948 | 12/2007 |
| WO | WO 2008042131 | 4/2008 |

OTHER PUBLICATIONS

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Newport Medical brochure, Introducing Newport HT70 Ventilator, obtained Feb. 1, 2010 at: http://www.medicare.ro/wp-content/uploads/2011/08/HT7O-VENTILATOR-SERIES-NEWPORT.pdf, brochure dated Sep. 2009, 9 pgs.

Newport Medical, New HT70 Ventilator Now Available, dated Sep. 2, 2010, obtained online at: http://www.newportnmi.com/ArticleDetail.asp?nArticleID=55, 2 pgs.

PCT International Search Report, Date of mailing Apr. 5, 2011, International 0 application No. PCT/US2010/058857, International filed Dec. 3, 2010, Applicant Nellcor Puritan Bennett LLC, 10 pgs.

Press Release, Newport Medical, HT70 Ventilator New Product Release, dated Aug. 12, 2010, obtained online at: http://mts.goexposoftware.com/2011/FORMfields/uploads/pressreleasescurprurl1301425003212296150.pdf, 1 page.

U.S. Appl. No. 12/760,725, Office Action mailed Dec. 6, 2012, 8 pgs.

U.S. Appl. No. 12/760,755, Office Action mailed Dec. 21, 2012, 14 pgs.

* cited by examiner

INTERACTIVE MULTILEVEL ALARM

RELATED APPLICATIONS

This application claims the benefit of U.S. Provisional Application No. 61/266,692, filed Dec. 4, 2009, which application is hereby incorporated by reference. This application also is related to application Ser. No. 12/760,755 entitled Alarm Indication System, and application Ser. No. 12/760,725, entitled Display of Historical Alarm Status.

INTRODUCTION

A ventilator is a device that mechanically helps patients breathe by replacing some or all of the muscular effort required to inflate and deflate the lungs. Ventilators also achieve a regulatory function during the ventilation process. A ventilator measures numerous physiological and operational parameters, including but not limited to exotic gas utilization, peak inspiratory pressure, battery failure and filter replacement. Depending on the status of the different parameters, it may be necessary for the ventilator to generate an alarm to indicate to the operator that attention is required.

Apparatus for an Interactive Multilevel Alarm

This disclosure describes embodiments of alarm systems and methods for use in devices such as medical ventilators. Embodiments described below provide for an apparatus of an interactive multilevel alarm system. Embodiments of the alarms also provide, at a glance, current alarm and device status information and historical alarm information to the operator. Embodiments also detect interaction with the alarm indicator by the operator. In some embodiments, additional visual indicators may be provided to identify non-normal or noteworthy operating conditions, such as the use of a therapeutic gas by a mechanical ventilator, so that the operator can assess the impact of that non-normal condition on the current and historical alarm information simultaneously provided.

In one aspect, this disclosure describes a method for interacting with an alarm system. The method provides a plurality of interactive indicators on the alarm system, in which the plurality of interactive indicators are visible in a 360 degree arc when viewed from a predetermined height. The method also identifies an alarm condition at one of the interactive indicators and generates an alarm indication associated with the detected alarm condition at the interactive indicator. The method further detects an operator's input at the interactive indicator and compares the type operator's input to a plurality of input types. The method also determines a type of input corresponding to the operator's input and modifies the alarm indication based on the type of input.

The disclosure also describes a ventilation system adapted to provide respiratory therapy to a patient. The ventilation system comprises a processor communicably coupled to a computer-readable medium that includes instructions executable by the processor. The instructions enable the processor to provide a plurality of interactive indicators on the alarm system, in which the plurality of interactive indicators are visible in a 360 degree arc when viewed from a predetermined height. The processor also identifies alarm condition with one of the interactive indicators and generates an alarm indication associated with the detected alarm condition via the interactive indicator. The processor further detects an operator's input at the interactive indicator and compares the type of the operator's input to a plurality of input types. The processor also determines a type of input corresponding to the operator's input and modifies the alarm indication based on the type of input.

The disclosure also describes an interactive alarm indication system for use on a ventilator. The interactive alarm system comprises one or more interactive indicators, in which each interactive indicator includes an interactive element and is visible in a 360 degree are around the interactive alarm indication system when viewed from a predetermined height. The one or more indicators include a current status indicator and a secondary indicator. The current status indicator is adapted to display a different color or a different combination of color and behavior based on a current status of the ventilator. The secondary indicator is adapted to display a different color or a different combination of color and behavior based on a highest historical status of the ventilator. The current status indicator and the secondary alarm indicator are further configured to identify an alarm condition and generate an alarm indication associated with the alarm condition. The indicators are also configured to detect an operator's input at the interactive element and compare the operator's input to a plurality of input types. The indicators are further configured to determine a type of input corresponding to the operator's input and modify the alarm indication based on the determined type of input.

These and various other features as well as advantages will be apparent from a reading of the following detailed description and a review of the associated drawings. Additional features are set forth in the description that follows and, in part, will be apparent from the description, or may be learned by practice of the described embodiments. The benefits and features will be realized and attained by the structure particularly pointed out in the written description and claims hereof as well as the appended drawings.

It is to be understood that both the foregoing general description and the following detailed description are exemplary and explanatory and are intended to provide further explanation of the claimed invention.

BRIEF DESCRIPTION OF THE DRAWINGS

The file of this patent contains at least one drawing executed in color. Copies of this patent or patent application publication with color drawing(s) will be provided by the Office upon request and payment of the necessary fee.

The following drawing figures, which form a part of this application, are illustrative of described technology and are not meant to limit the scope of the invention as claimed in any manner, which scope shall be based on the claims appended hereto.

FIG. 2 is a front view of the display showing the four indicators.

FIG. 3 is an oblique front view of the display showing the four indicators.

FIG. 4 is a side view of the display showing the four indicators.

FIG. 5 is an oblique rear view of the display showing the four indicators.

FIG. 6 is a rear view of the display showing the four indicators.

DETAILED DESCRIPTION

Figure 1:
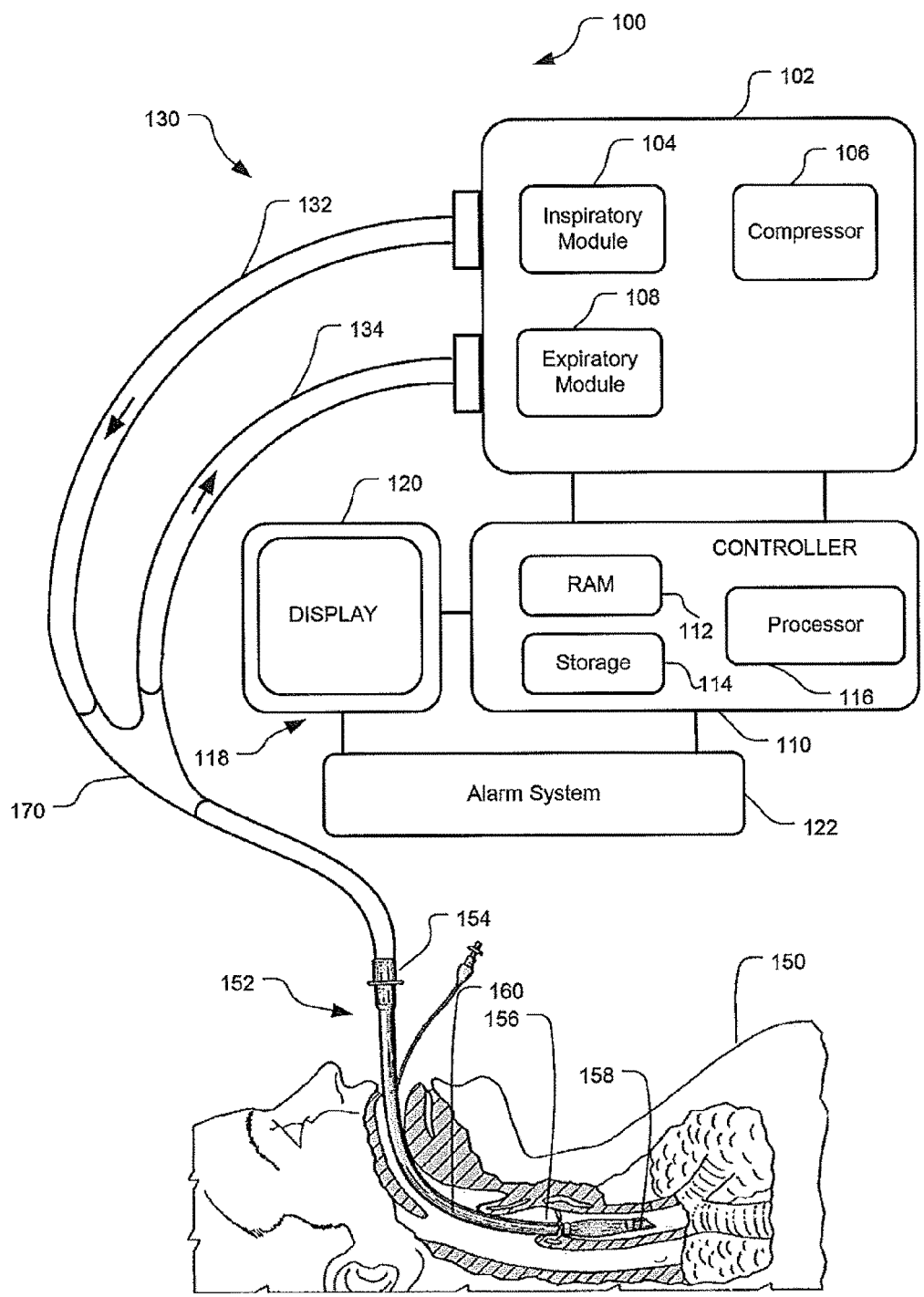
FIG. 1 depicts a ventilator used during mechanical ventilation of a patient.

Although the techniques introduced above and discussed in detail below may be implemented for a variety of devices, the present disclosure will discuss the implementation of these techniques for use in a mechanical ventilator system for use in providing ventilation support to a human patient. The reader will understand that the technology described in the context of a medical ventilator for human patients could be adapted for use with other systems such as ventilators for non-human patients, different types of medical devices and any devices that can generate multiple alarms or operate in one or more of multiple different states.

Medical ventilators monitor the delivery of breathing gas to the patient, may directly or indirectly monitor physiological parameters of the patient, and monitor the operation of the ventilator. For the purposes of this discussion, the ventilator will be referred to as including an interactive multilevel alarm system as a way of collectively talking about those elements in the control systems of the ventilator that generate alarms based on the various parameters monitored by the ventilator. The interactive multilevel alarm system includes a visible alarm display system and may include an audible alarm generating system. The visible alarm display system refers to those components (e.g. visible indicators) other than the graphical user interface of the ventilator that provide visible indications of alarms and ventilator status information to the operator. Likewise, the audible alarm system refers to those components (e.g. speakers and sound generators) responsible for generating audible alarms.

The interactive multilevel alarm system indicates the current status level of the ventilator at a current status indicator. The current status indicator may be located on the ventilator such that the operator may be able to see the current status indicator from any side or angle. Depending on the settings provided, selected therapy and other conditions, a ventilator may be designed to generate some number of alarms of different magnitudes based on the current status level. Alarms of different magnitudes may be grouped into arbitrary "levels" dictated by the urgency or level of response deemed necessary by operators or by some characteristic. For example, in the embodiments described in this disclosure, at any given time while providing therapy to a patient a ventilator may be in one of four different current conditions.

A "no current alarm" or normal operation status level;
A low-level alarm condition;
A medium-level alarm condition;
A high-level alarm condition.

Different current status levels displayed at the current status indicator indicate to the operator that a different response is needed and different visual and audible alarms may be associated with each status level. For example, a low-level alarm may require no immediate attention but is provided for informational purposes only. A medium-level alarm may indicate that the operator should evaluate the conditions that caused the alarm in order to determine if an action is necessary. A high-level alarm condition may indicate a life-threatening or other emergency that requires immediate attention.

For example, a low-level alarm may be generated when a measured parameter, such as peak inspiratory pressure observed in a patient during breathing, exceeds a threshold amount (an example of patient physiological parameter being outside the targeted range); when a battery has failed, a condensate collection cup is full or a filter needs replacing (an example of an alarm being generated based on an operational condition.) Similarly, the low level alarm may be "escalated" to a medium level alarm if the measured parameter is observed to be in excess of the threshold for a predetermined period of time. If the patient's total exhaled tidal volume was to drop below the set point or the ventilator determines that the patient has become disconnected from the ventilator, a high-level alarm may be initiated. Escalation will be discussed further herein.

FIG. 1 illustrates an embodiment of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive patient interface 152.

Ventilation may be achieved by invasive or non-invasive means. Invasive ventilation, such as invasive patient interface 152, utilizes a breathing tube, particularly an endotracheal tube (ET tube) or a tracheostomy tube (trach tube), inserted into the patient's trachea in order to deliver air to the lungs. Non-invasive ventilation may utilize a mask or other device placed over the patient's nose and mouth. For the purposes of this disclosure, an invasive patient interface 152 is shown and described, although the reader will understand that the technology described herein is equally applicable to any invasive or non-invasive patient interface.

Airflow is provided via ventilation tubing circuit 130 and invasive patient interface 152. Ventilation tubing circuit 130 may be a dual-limb (shown) or a single-limb circuit for carrying gas to and from the patient 150. In a dual-limb embodiment as shown, a "wye fitting" 170 may be provided to couple the patient interface 154 to an inspiratory limb 132 and an expiratory limb 134 of the ventilation tubing circuit 130.

Pneumatic system 102 may be configured in a variety of ways. In the present example, system 102 includes an expiratory module 110 coupled with the expiratory limb 134 and an inspiratory module 104 coupled with the inspiratory limb 132. Compressor 106 or another source(s) of pressurized gases (e.g., air, oxygen, and/or helium) is coupled with inspiratory module 104 to provide a gas source for ventilatory support via inspiratory limb 132.

The pneumatic system may include a variety of other components, including sources for pressurized air and/or oxygen, mixing modules, valves, sensors, tubing, accumulators, filters, etc. Controller 112 is operatively coupled with pneumatic system 102, signal measurement and acquisition systems, and an operator interface 120 may be provided to enable an operator to interact with the ventilator 100 (e.g., change ventilator settings, select operational modes, view monitored parameters, etc.). Controller 110 may include memory 114, one or more processors 118, storage 116, and/or other components of the type commonly found in command and control computing devices.

The memory 112 is computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The controller 110 issues commands to pneumatic system 102 in order to control the breathing assistance provided to the patient by the ventilator. The specific commands may be based on inputs received from patient 150, pneumatic system 102 and sensors, operator interface 118 and/or other components of the ventilator. In the depicted example, operator interface includes a display 120 that is touch-sensitive, enabling the display to serve both as an input and output device.

As depicted, the alarm system 122 is communicatively connected to the controller 110. The controller 110 of the ventilator can direct the alarm system 122 to generate alarms under predetermined circumstances. Different predetermined circumstances can cause the controller 110 to communicate different alarm levels to the alarm system 122. The different alarm levels communicated by the controller 110 cause the alarm system 122 to display different alarm statuses on alarm system indicators as described herein. The controller 110 also communicates to the alarm system 122 whether the ventilator is delivering an exotic gas to the patient. Delivery of an exotic gas is also displayed by the alarm system 122 on an alarm system indicator as described herein.

The alarm system 122 is also communicatively connected, either directly or indirectly, to the display 120. When the alarm system 122 detects an operator's input, the alarm system 122 causes the display 120 to display alarm conditions.

Figure 2:
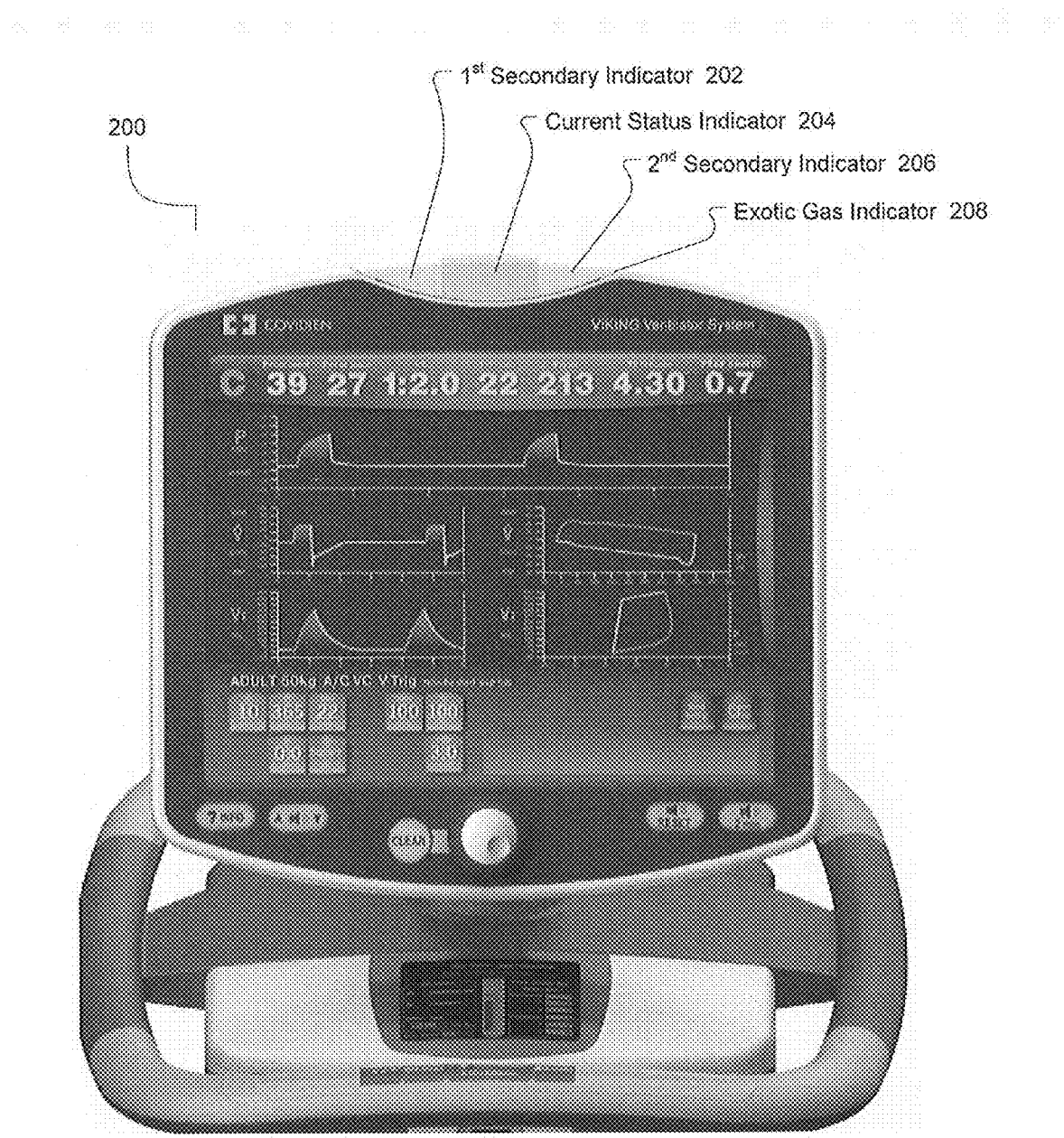
FIGS. 2-6 provide different views of a ventilator having a display and built into the top of the display housing a four indicator visual alarm system comprising a lower, exotic gas indicator, a first and a second secondary indicator and a current status indicator.

FIG. 2 illustrates an embodiment of a visible alarm display system 200. The visual alarm display system 200 includes alarm lights, referred to herein as indicators. The visible alarm display system includes a current status indicator 204, a secondary indicator, in this embodiment made up of a first secondary indicator 202 and a second secondary indicator 206, and an exotic gas indicator 208. The indicators may include one or more of any type including incandescent lights, light emitting diodes (LEDs), or other technology capable of creating visually perceptible light.

The general operation of the current status indicator 204 has already been discussed. The secondary indicator, which in the embodiment shown consists of two non-contiguous zones 202 and 206, indicates the highest historical alarm level. The highest historical alarm level reflects the highest current status level reached since the alarm was last reset. Thus, an operator viewing the secondary indicator 202 and 206 will instantly know if the ventilator has in the past been in an alarm state regardless of its current status. Depending on the embodiment, the secondary indicator 202 and 206 may indicate only the existence of a historical alarm state higher than the current status of the ventilator. In other words, the secondary indicator 202 and 206 will display the current status level if the current status level is equal to or higher than the highest historical status level. The secondary indicator 202 and 206 may also be referred to as a "latched indicator" to allude to its function as latching to the highest alarm level seen by the ventilator since the last time the alarm system was reset by the operator or the ventilator was powered up.

The secondary indicator 202 and 206 in the illustrated embodiment highlights that in the three indicator alarm described herein, any of the indicators (i.e., the current status indicator, the secondary alarm indicator and the exotic gas indicator) may consist of separate individual indicators or zones that act together so that at least one zone of each indicator is visible from all angles. When discussing embodiments in which an indicator (i.e., the current status indicator, the secondary alarm indicator and the exotic gas indicator) has multiple, non-contiguous zones, the different zones will be referred to as a "first" indicator and "second" indicator of that particular type (e.g., the first current status indicator and second current status indicator), although the reader will understand that the first and second indicators may also be referred to collective as a single indicator (e.g., the current status indicator may consist of a first and second current status indicator).

In the embodiment shown, for instance, the visual display system includes a first secondary indicator 202 and a second secondary indicator zone 206. The first secondary indicator 202 and the second secondary indicator 206 flank either side of the current status indicator 204. In an embodiment, the current status indicator 204 and secondary indicator 202 and 206 are located on the ventilator such that, when viewed from predetermined heights such as heights above 4 feet above the floor on which the ventilator is standing, at least one secondary indicator is visible from any direction in a 360 degree arc around the ventilator. That is, regardless of the relative angle of the operator to the ventilator (e.g., facing the ventilator from the front, back, sides, etc.) at least one of the two secondary indicators will be in view.

In the embodiments shown herein, this is achieved by placing the indicators, with the current status indicator 204 above and the secondary indicator below 202 and 206, on top of the highest point of the ventilator. Other configurations are also possible including providing multiple indicators at multiple locations around the housing of the ventilator or providing indicators in the form of bands running around the exterior of the ventilator at different heights.

In one embodiment, the current status indicator 204 and the secondary indicators 202 and 206 are touch sensitive. Detection of an operator's touch to either indicator is considered acknowledgement by a user to address the alarm condition. In an embodiment, such an acknowledgement may cause the alarm system to lower the volume, display specific windows or information on the display or cease the emission of an audible alarm associated with the current ventilator status level.

The interactive element may be able to differentiate between different types of inputs from the operator, such as differentiating between a tap, a touch starting from the left and going to the right and a touch starting from the right and going to the left. Depending on what type of input is received, the audible alarm may be modified in different ways. For example, a tap may silence the alarm, a longer touch may pull up a particular window on the display related to the alarm and a left-to-right or right-to-left touch may make the alarm louder or quieter.

Different interactive elements may be provided for the audible alarm control and for the visual alarm control. For example, touching the current status indicator 204 may control the audible alarm and touching the secondary indicator 202 and 206 may clear the historical status level so that the historical status level is reset to the current status level. In yet another embodiment, the operator could bring up a control panel/cause the ventilator to display a graphical user interface associated with the alarm condition by touching the current status indicator 204 or secondary indicator 202 and 206.

The interactive element may use any suitable technology or device in order to detect the operator command. For example, in an embodiment an indicator may incorporate a mechanical push switch so that the indicator can be depressed by the operator's finger. Alternatively, a touch-sensitive technology such as resistive, capacitive, acoustic pulse recognition or any other technology, now known or later developed, for detecting a user input. In an embodiment the entire display housing including the visual indicators could be covered by a material, such as a glass or polymer to create a unitary, smooth exterior surface into which different interactive elements are located in different areas of the cover material. Thus, different areas of the housing surface including the surface of the visual indicators could be used as interface elements.

In yet another embodiment, additional interactive elements may be provided at various locations on the ventilator for interacting with the alarm system and controlling the audio and visual alarms. For example, when an audible alarm is active an interactive element for controlling volume may appear or be illuminated so that the operator is alerted to the location of the element. As another example, the current status indicator 204 could be one interactive element that silences the audible alarm and another interactive element could be located somewhere else on the ventilator to control the volume of the audible alarm, such as on the main ventilator display.

The visible alarm display system may also include an exotic gas indicator 208. In an embodiment, the exotic gas indicator 208 can be viewed from any position around the ventilator. For example, in one embodiment, each of the three indicators (current status, secondary and exotic gas) are stacked, one on top of the other, and placed on top of the highest component of the ventilator. The exotic gas indicator 208 may be off until such time as an exotic gas is in use. In an embodiment, the exotic gas indicator 208 may use a different color or color/behavior combination for each different exotic gas so that the operators know which gas is in use. Alternatively, a single color may be used in which the gas in use cannot be determined from the indicator. Likewise, the exotic gas indicator 208 may be adapted to also indicate specific ranges of oxygen concentrations, for example lighting when a gas mix setting such as oxygen drops below or exceeds an operator set limit. Such an indication could be used to note a change in the patient's status. In another embodiment, the exotic gas indicator can display different colors to indicate different exotic gasses used during ventilation.

An interactive element may also be incorporated into the exotic gas indicator 208. In an embodiment, for example, an operator could disable the delivery of the exotic gas by touching the exotic gas indicator 208. Alternatively, the operator could bring up a control panel/cause the ventilator to display a graphical user interface associated with and/or controlling the exotic gas delivery by touching the exotic gas indicator 208. Such an interactive element may or may not be disabled when there is no exotic gas being delivered.

Figure 3:

FIG. 3 depicts the visual alarm display system 300 from an oblique view. As can be seen, the current status indicator 304, first secondary indicatory 302, second secondary indicator 306, and exotic gas indicator 308 are all visible from the side angle.

Figure 4:
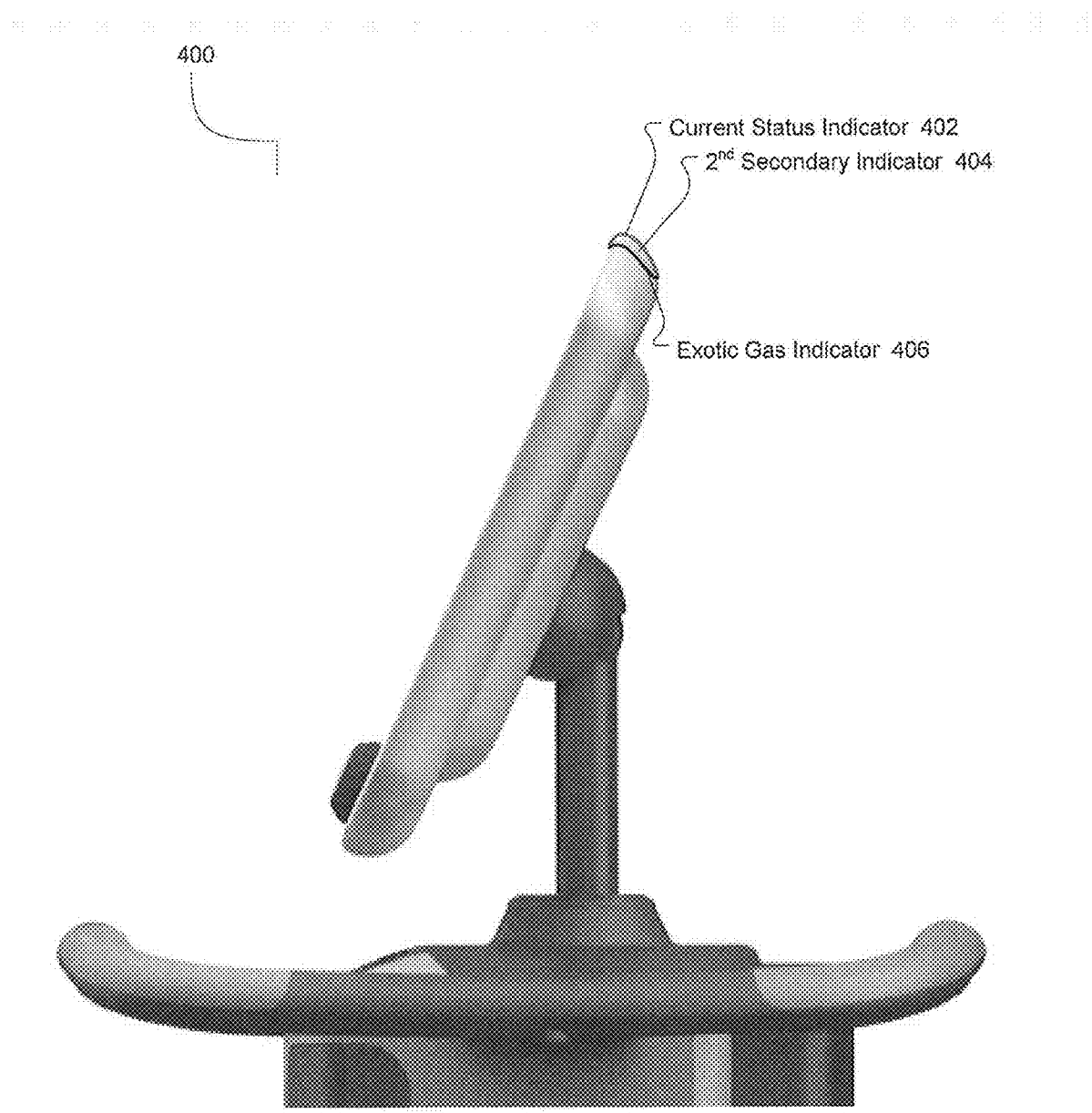

FIG. 4 depicts the visual alarm display system 400 from a side view. As can be seen, the current status indicator 402, second secondary indicator 404, and exotic gas indicator 406 are all visible from the side.

Figure 5:
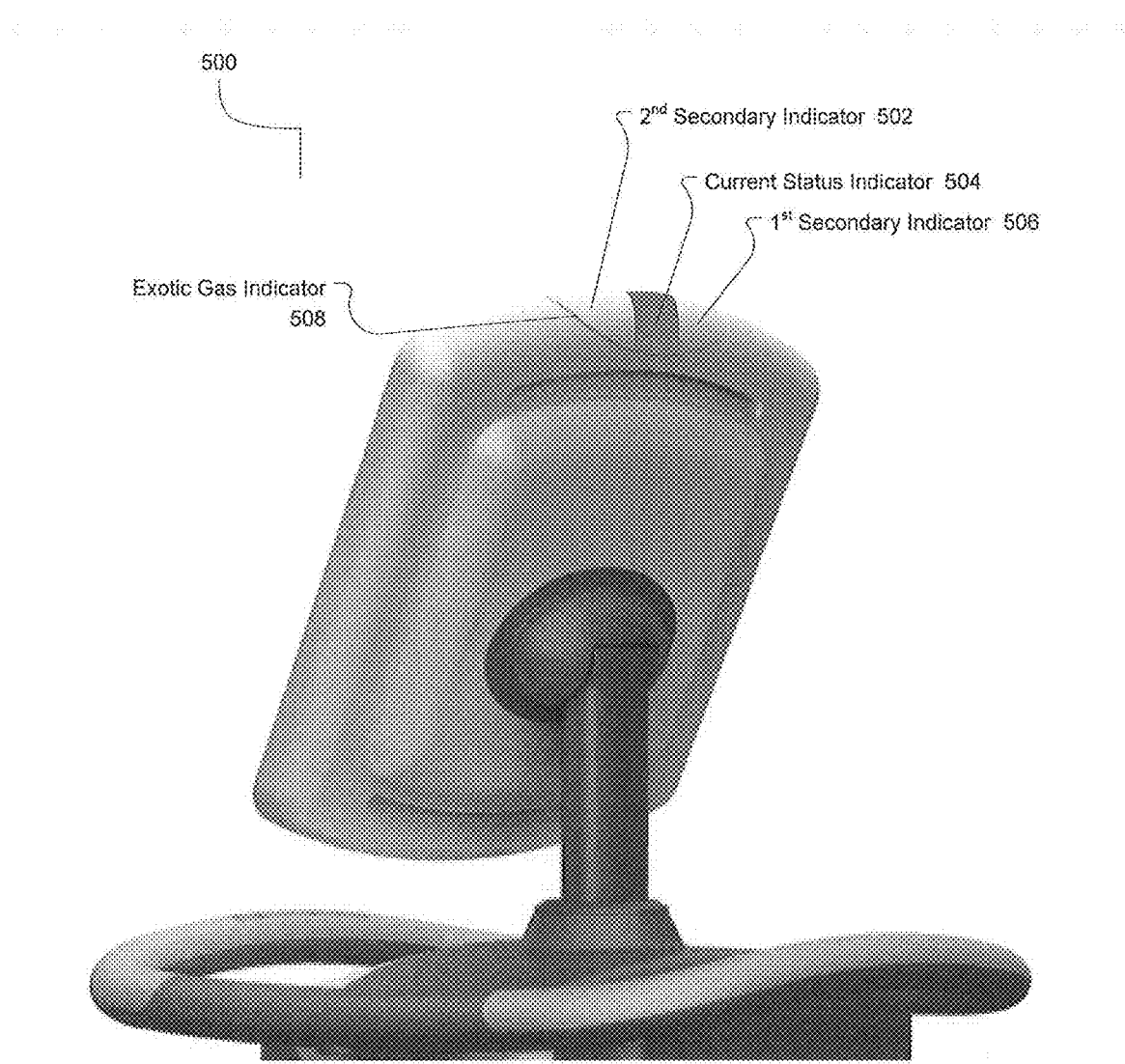

FIG. 5 depicts the visual alarm display system 500 from an oblique rear view. As can be seen, the current status indicator 504, first secondary indicator 506, second secondary indicator 502, and exotic gas indicator 508 are all visible from the back angle.

Figure 6:
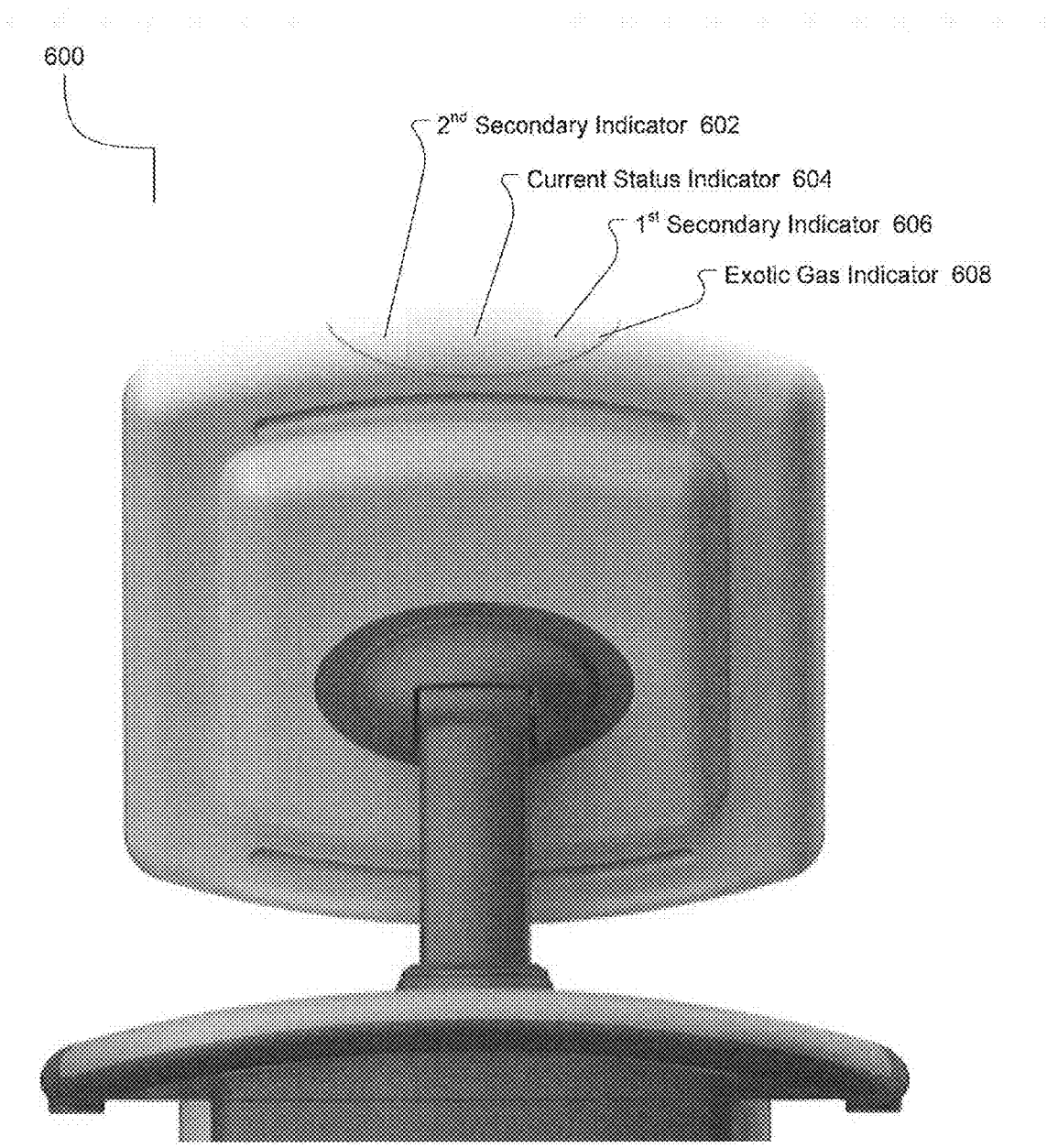

FIG. 6 depicts the visual alarm display system from 600 a rear view. As can be seen, the current status indicator 604, first secondary indicator 606, second secondary indicator 602, and exotic gas indicator 608 are all visible from the back.

Figure 7:
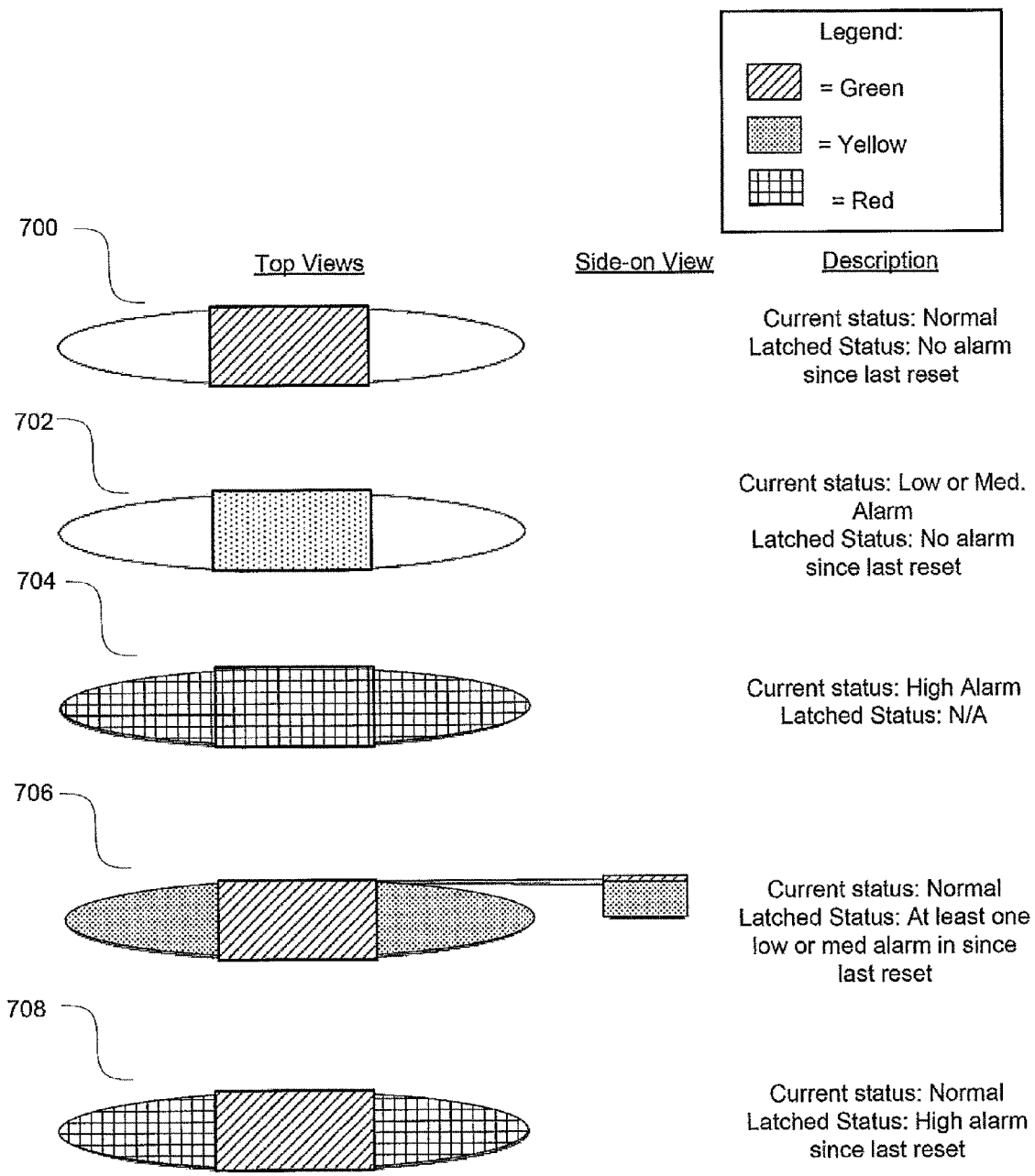
FIG. 7 depicts different ventilation urgency levels communicated by different colors of light or combinations of light and behavior displayed by the indicators. The illustrations are top views of only the current status and secondary indicators showing the different color schemes for an embodiment of operation. One side view is also shown.

FIG. 7 depicts different ventilation urgency levels communicated by different colors of light displayed by the indicators. In one embodiment, any of the indicators are able to emit different colors of light for different urgency levels. Indicators may also be able to flash or strobe in order to attract more attention under certain circumstances. The following table describes an embodiment of the indicators' different colors and behavior during different status levels and de-escalation scenarios.

| Ventilator's Current Status | Current Status Indicator | Secondary Indicator |
| --- | --- | --- |
| Normal Status | Green | Color indicative of highest historical alarm status (i.e., yellow, flashing yellow or red); off or green if highest historical status is normal. |
| Low-level alarm | Yellow | Yellow or highest historical alarm status if higher than low-level alarm. |
| Medium-level alarm | Flashing Yellow | Yellow or Red if highest historical alarm status is high-level alarm. |
| High-level Alarm | Flashing Red | Red or Flashing Red |

The following table describes another embodiment of the indicators' different colors and behavior during different status levels and de-escalation scenarios.

| Ventilator's Current Status | Current Status Indicator | Secondary Indicator |
| --- | --- | --- |
| Normal Status | Green | Color indicative of highest historical alarm status (i.e., yellow, flashing yellow or red); off if highest historical status is normal. |
| Low-level alarm | Yellow | Color indicative of highest historical alarm status (i.e., yellow or red); off if highest historical status is normal. |
| Medium-level alarm | Flashing Yellow | Color indicative of highest historical alarm status (i.e., yellow or red); off if highest historical status is normal. |
| High-level Alarm | Flashing Red | Flashing Red |

A series of exemplary multilevel alarm scenarios are depicted in FIG. 7. Alarm scenario 700 depicts an alarm with a current status of normal, as indicated by the green current status indicator. The secondary status indicator of alarm scenario 700 does not display any color. This indicates that alarm scenario 700 has no historical status. The latched status of alarm scenario 700 is that no alarm has been activated since the alarm was last reset.

Alarm scenario 702 depicts an alarm with a current status of low or medium, as indicated by the yellow current status indicator. The secondary status indicator of alarm scenario 702 does not display any color. This indicates that alarm scenario 702 has no historical status. The latched status of alarm scenario 702 is that no alarm has been activated since the alarm was last reset.

Alarm scenario 704 depicts an alarm with a current status of high, as indicated by the red current status indicator. The secondary status indicator of alarm scenario 704 also displays red. This indicates that alarm scenario 704 has a current status equal to the highest historical status. The latched status of alarm scenario 704 is not applicable because the current status of the alarm scenario is the same as the highest historical status.

Alarm scenario 706 depicts an alarm with a current status of normal, as indicated by the green current status indicator. The secondary status indicator of alarm scenario 706 displays yellow. This indicates that alarm scenario 706 has a highest historical status of low or medium. The latched status of alarm scenario 706 is that the alarm scenario has displayed a low or medium alarm status since the alarm was last reset. FIG. 7 also depicts a side view of alarm scenario 706. As can be seen, both the current status indicator and the secondary status indicator are visible from the side of the alarm system, with the current status indicator located on top of the secondary indicator.

Alarm scenario 708 depicts an alarm with a current status of normal, as indicated by the green current status indicator. The secondary status indicator of alarm scenario 708 displays red. This indicates that alarm scenario 708 has a highest historical status of high. The latched status of alarm scenario 708 is that the alarm scenario has displayed a high alarm status since the alarm was last reset.

Figure 8:
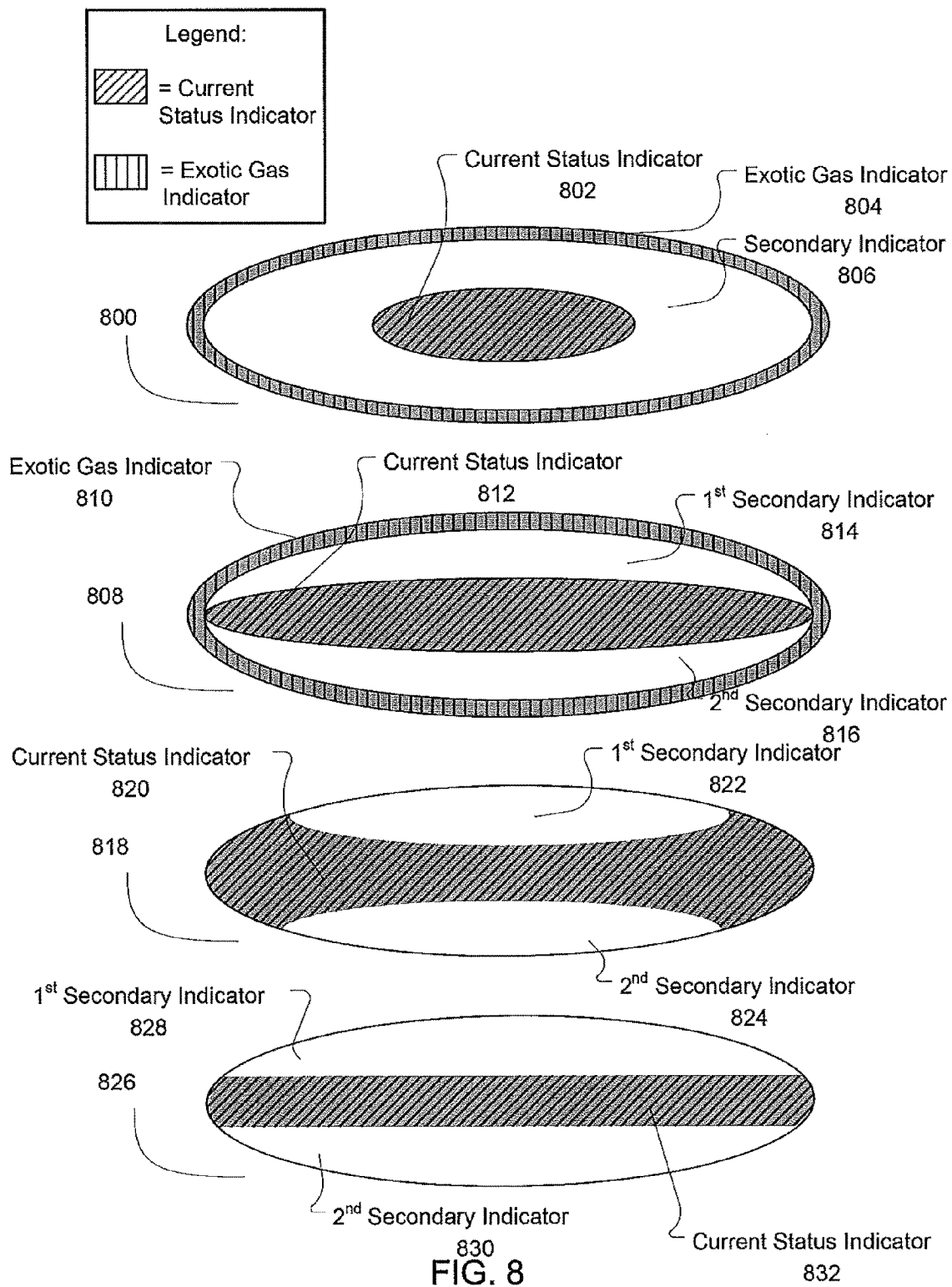
FIG. 8 depicts different visual combinations of the different indicators of the interactive multilevel alarm system from a top view.

FIG. 8 depicts different visual combinations of the different indicators of interactive multilevel alarm system from a top view. Combination 800 depicts an elliptical current status indicator 802 surrounded by an elliptical secondary indicator 806. The secondary indicator 806 is surrounded by an elliptical exotic gas indicator 804.

Combination 808 depicts an elongated elliptical current status indicator 812. The current status indicator is flanked by a first secondary indicator 814 and a second secondary indicator 816. The current status indicator 812, first secondary indicator 814, and second secondary indicator 816 are surrounded by an elliptical exotic gas indicator 810. In this embodiment, the first and second secondary indicators 814, 816 operate in unison and can be considered single embodiment of a secondary indicator that can be viewed from all angles.

Combination 818 depicts a visual alarm that does not include an exotic gas indicator. The current status indicator 820 separates the first secondary indicator 822 from the second secondary indicator 824. As depicted, the ends of the current status indicator 822 are wider than the mid section of the current status indicator 822.

Combination 826 also depicts a visual alarm display that does not include an exotic gas indicator. The current status indicator 820 separates the first secondary indicator 822 from the second secondary indicator 824.

Figure 9:
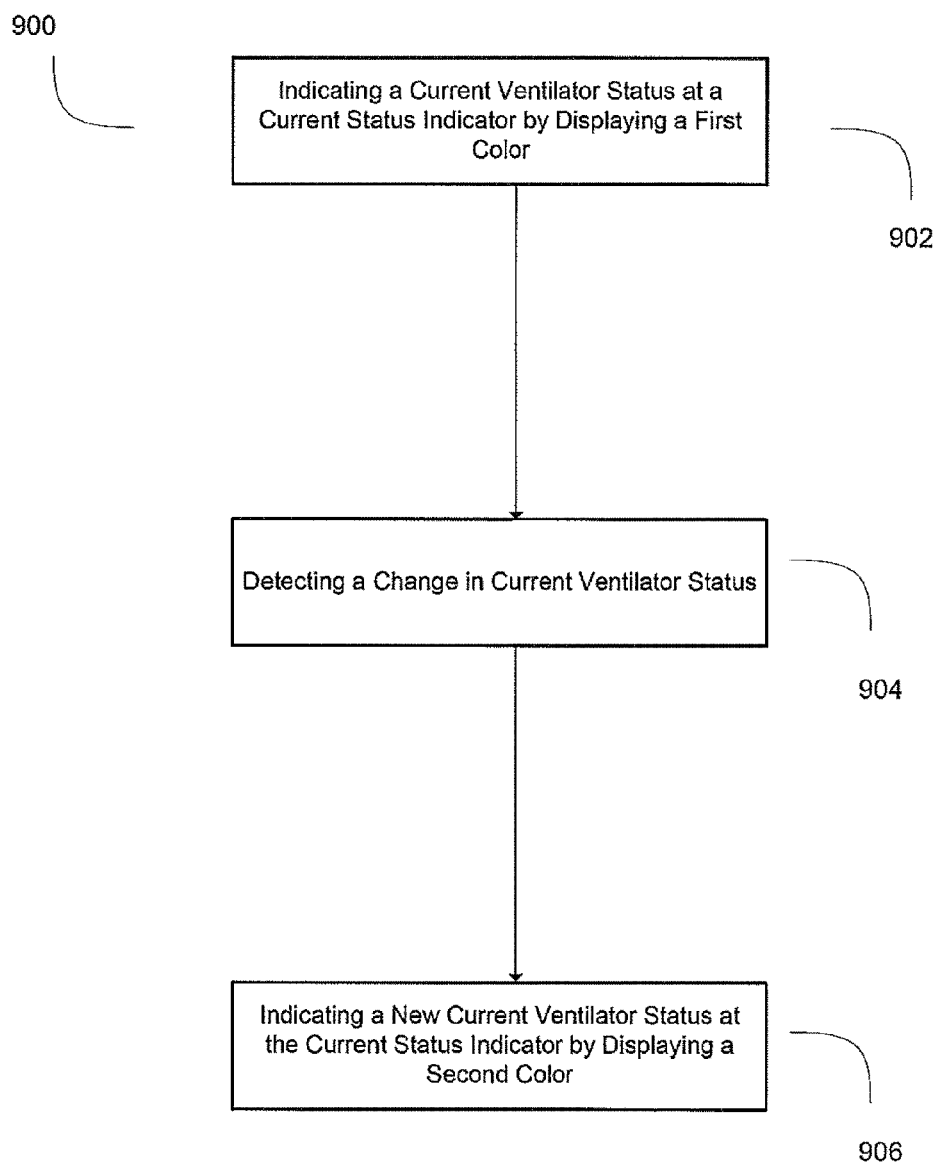
FIG. 9 depicts a method of escalation or de-escalation in current indicator status.

FIG. 9 depicts a method 900 of escalating or de-escalating the alarm level associated with the current ventilator status. At indicating operation 902, the interactive multilevel alarm system indicates a current ventilator status by displaying a first color at a current status indicator. The multilevel alarm system can also indicate a current ventilator status by displaying a first combination of color and behavior at a current status indicator. In one embodiment, the current ventilator status is an alarm level. The different alarm levels can indicate to an operator that a different response is needed. Exemplary alarm levels include: a "no current alarm" or normal operation status level, a low-level alarm condition, a medium-level alarm condition, and a high level alarm condition. Each of the exemplary alarm levels can be associated with a different color or different combination of color and behavior as discussed above.

At detecting operation 904, the multilevel alarm system detects a change in current ventilator status. The change in current ventilator status can be either an escalation or de-escalation. An escalation occurs when the alarm level associated with the current ventilator status increases. For example, current ventilator status escalates when the alarm level increases from low to medium. A de-escalation occurs when the alarm level associated with the current ventilator status decreases in alarm level. For example, current ventilator status de-escalates when the alarm level decreases from medium to low.

At indicating operation 906, the multilevel alarm system indicates a new current ventilator status at the current status indicator by displaying a second color. The multilevel alarm system can also indicate a new current ventilator status by displaying a second combination of color and behavior at the current status indicator. The second color or second color and behavior combination is associated with the escalated alarm level or the de-escalated alarm level. As will be discussed in greater detail below, if there is an escalation, the secondary indicator will be changed if the new status is greater than what is currently displayed by the secondary indicator and, if there is a de-escalation, there will be no change in the status of the secondary indicator.

Figure 10:
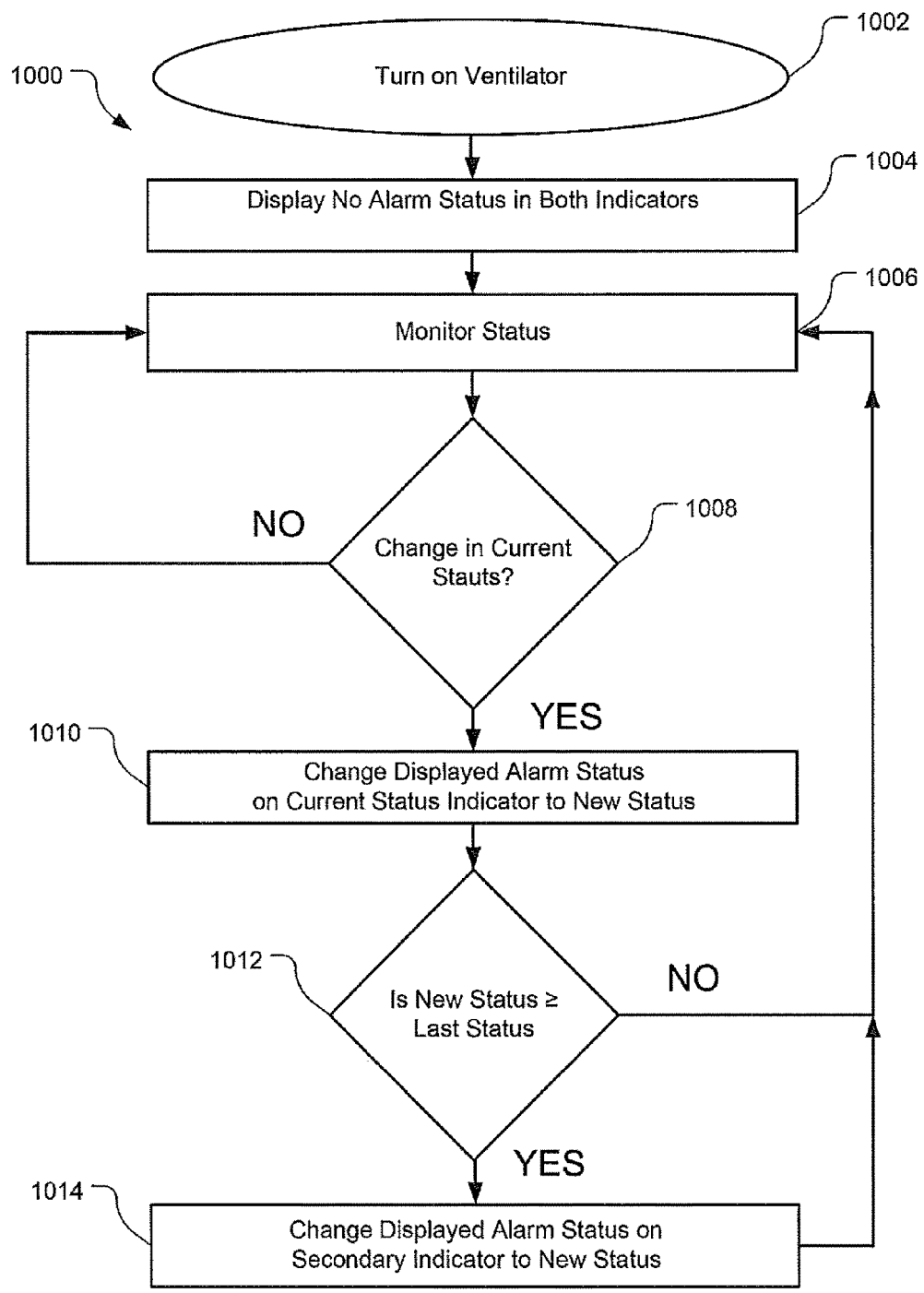
FIG. 10 depicts a method of indicating a highest historical ventilator system status at a secondary indicator.

FIG. 10 depicts a method 1000 of indicating a highest historical ventilator system status at a secondary indicator. At turn on operation 1002, the ventilator is turned on. Turning on can be accomplished by plugging the ventilator in, depressing an "on" switch, awaking the ventilator from sleep mode, or any other known method for turning on a machine.

At display operation 1004 the alarm system indicates an initial "no alarm" status at both indicators. A "no alarm" is displayed because the ventilator is yet to communicate a predetermined alarm condition to the alarm system that would cause the alarm system to display an alarm. The "no alarm" status is indicated on both the current status indicator and secondary indicator. The current status indicator and secondary indicator indicate a "no alarm" status by displaying a color or combination of color and behavior at the current status indicator and secondary indicator. As discussed with reference to FIG. 9, the color or combination of color and behavior is associated with an alarm level indicating the patient's "no-alarm" ventilatory status.

At monitor operation 1006, the multilevel alarm system monitors the ventilatory status of the patient. As discussed above, the alarm system is communicatively coupled to the controller. The alarm system monitors the ventilatory status of the patient by communicating with the controller and waiting for a change in status.

At change operation 1008, the multilevel alarm system awaits a change in current ventilatory status of the patient. As discussed above, this change is detected from communication with the controller during the monitoring operation 1006. As discussed with reference to FIG. 9, the change in ventilator status can be an escalation or de-escalation in alarm level. If a change in current status is not detected, the method 1000 returns to monitor operation 1006. If a change in current status is detected, the method 1000 advances to change current status operation 1010.

At change current status operation 1010, the alarm status displayed by the current status indicator is changed to indicate a new current status. A new current status is indicated by displaying a new color or new combination of color and behavior at the current status indicator. As discussed with reference to FIG. 9, the new current status color or new current status combination of color and behavior is associated with the escalated alarm level or the de-escalated alarm level.

At compare operation 1012, the new current status is compared to the last highest current status. The multilevel alarm system compares the new current status to the last highest current status to determine whether the new current status is greater than or equal to the last highest current status. The new current ventilator status is greater than or equal to the last highest current status if the alarm level of the new current ventilator status is greater than or equal to the alarm level of the last highest current status. For example, if the new current ventilator status is "medium" and the last highest current status was "medium", "low", or "normal", then the new current status is greater than or equal to the last highest current status. On the other hand, if the new current status is "medium" and the last highest current status was "high", then the current status is less than the last highest current status.

If, at compare operation 1012, the multilevel alarm system determines that the new current status is less than the last current status, the secondary alarm level is maintained. This is because under this process flow, the secondary alarm level will only be maintained when the current alarm level is less than a previous alarm level or levels. The method 1000 then returns monitor operation 1006.

If at compare operation 1012, the multilevel alarm system determines that the new current status is greater than or equal to the last highest current status, an upgrade secondary alarm operation 1014 is performed. In operation 1014, the multilevel alarm system displays the new current status color or the new current status combination of color and behavior at the secondary indicator to indicate the highest historical ventilator system status. Since the multilevel alarm system has not activated an alarm greater than the current status level, the secondary indicator displays the same color or the same combination of color and behavior as the current status indicator.

Figure 11:
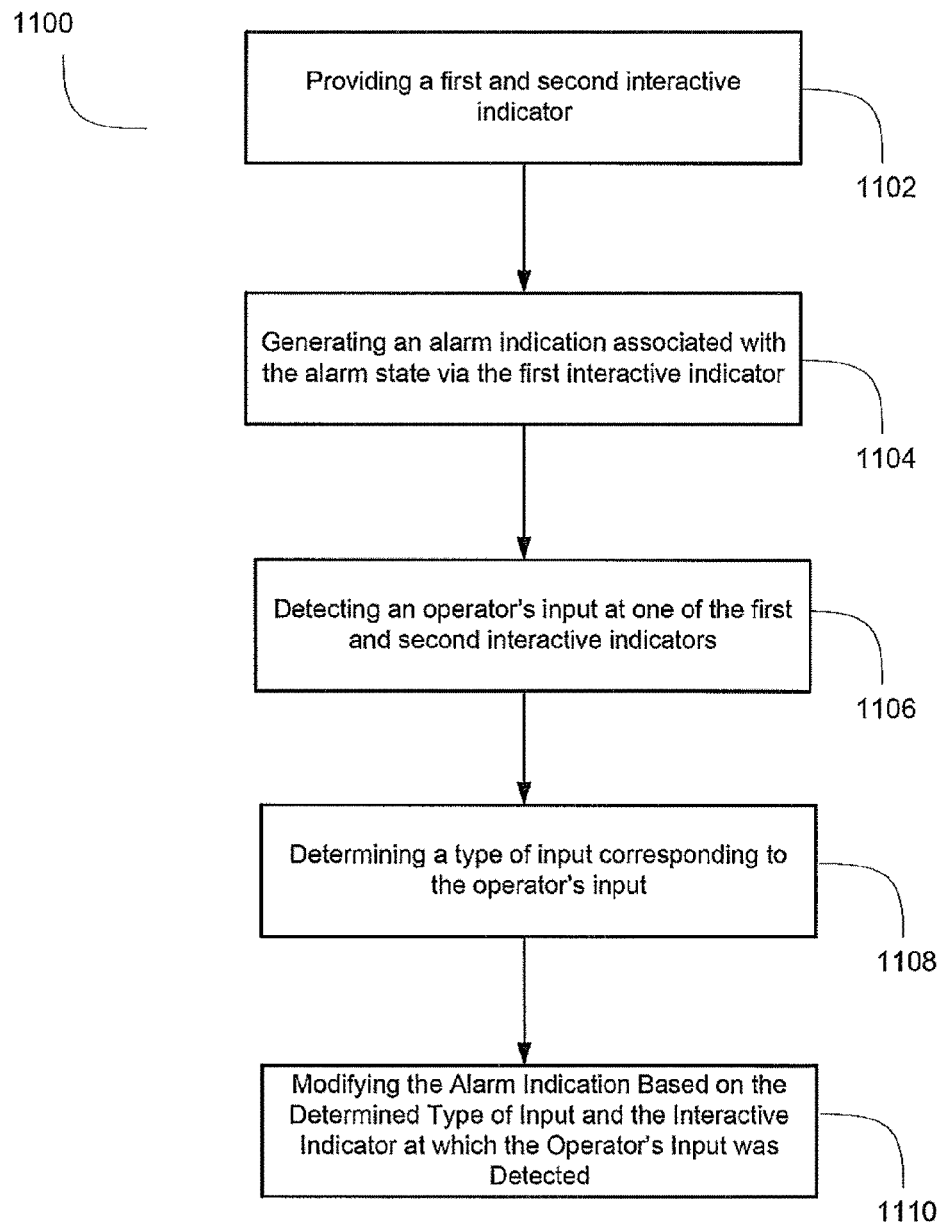
FIG. 11 depicts a method for providing interactivity with the multilevel alarm system of the ventilator by making one or more of the indicators an interactive element.

FIG. 11 depicts a method 1100 for providing interactivity with the interactive multilevel alarm system of the ventilator when the alarm is in an alarm state. At provide operation 1102, the alarm system provides a first and second interactive indicator. In one embodiment, the first and second interactive indicator are visible in a 360 degree arc when viewed from a predetermined height. As discussed previously, the first interactive may be a current status indicator and the second interactive indicator may be a secondary indicator. The first and second interactive indicators can further be comprised of multiple zones.

At generate operation 1104, the alarm system generates an alarm indication associated with the alarm state via the first interactive indicator. As discussed above, the alarm condition may be a visual indicator associated with the alarm state. For example, and alarm state of "high" is associated with a red visual indicator. In this embodiment, the first interactive indicator would display a red light. In another embodiment, the alarm indication is an audible alarm associated with an alarm state. In another embodiment, the alarm indication includes a combination of audible and visual alarms.

At detect operation 1106, the alarm system detects an operator's input at one of the first and second interactive indicators. In one embodiment, one or more of the indicators are touch sensitive and the alarm system detects an operator's touch. In another embodiment, the indicator may be a simple push switch that can be depressed by an operator's finger. In another embodiment, the operator's input is detected at a different indicator than the indicator generating the alarm indication.

At determine operation 1108, the alarm system determines a type of input corresponding to the operator's input. In one embodiment, the type of input might be a tap. In another embodiment, the type of input might be a touch starting from the left and going to the right. In another embodiment, the type of input might be a touch starting from the right and going to the left.

At modify 1110, the alarm system modifies the indicator alarm based on the determined type of input and the interactive indicator at which the operator's input was detected. In one embodiment, if the alarm system determines that the type of input is a tap on the current status indicator, the alarm system may adjust the audible alarm. In another embodiment, if the alarm system determines that the type of input is a tap on the secondary indicator, the alarm system may clear the historical status level so that the historical status level is rest to the current status level. In an alternative embodiment, the interaction with the alarm indicators may not affect the indicator's condition, but rather may change the audible alarm or perform some other function. In another embodiment, if the alarm system determines that the input was received at a first indicator, it may modify the alarm indication at both the first and second indicators. In another embodiment, if the alarm system determines that the input was received at the second indicator, it may only modify the alarm condition at the second indicator.

In yet another embodiment, the operator could bring up a control panel/cause the ventilator to display a graphical user interface associated with the alarm condition by touching the current status or secondary indicator. For example, touching the secondary indicator could bring up a historical log of alarms and identify which condition or occurrence resulted in the secondary indicator being escalated to its current alarm state. For example, if the secondary indicator is latched on a medium alarm, the operator could press the secondary indicator and be immediately presented with the alarm log showing the first (or every) medium alarm event that has occurred since the last alarm reset. In addition to the alarm log, other windows associated with an alarm may also be presented in response to an indicator touch. In an embodiment, if the alarm is associated with a specific setting on the ventilator, a window could also be displayed allowing the operator immediate access to the setting. Similarly, if the alarm is associated with a specific patient physiological parameter (e.g., minute volume, respiration rate, etc.), a window could be presented showing the historical data which caused the alarm.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such as a way as to be performed by a different module or method step without deviating from the overall disclosure. In other words, functional elements being performed by a single or multiple components, in various combinations of hardware and software, and individual functions can be distributed among software applications. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for interacting with an alarm system when the alarm system is in an alarm state, the method comprising:
   providing a first and second interactive indicator, the first and second interactive indicators visible in a 360 degree arc when viewed from a predetermined height;
   generating an alarm indication associated with the alarm state via the first interactive indicator, wherein the alarm indication includes lighting the first interactive indicator;
   detecting an operator's input at one of the first and second interactive indicators, wherein the operator's input is a direct interaction at one of the first and second interactive indicators;
   determining a type of input corresponding to the operator's input; and
   modifying the alarm indication based on the determined type of input and the interactive indicator at which the operator's input was detected.

2. The method of claim 1, wherein the modifying operation further comprises lowering the volume from an audible alarm.

3. The method of claim 1, wherein the modifying operation further comprises ceasing emission of an audible alarm.

4. The method of claim 1, wherein the detecting operation further comprises a type of input selected from: detecting a tap, or detecting a touch starting from one side of the indicator and going to the other side to the other side of the indicator 5. The method of claim 1, wherein the detecting operation detects the operator's input at an interactive element of the one interactive indicator, the interactive element selected from one of: a push switch or touch-sensitive technology.

6. The method of claim 1, wherein the modifying operation further comprises resetting the alarm.

7. The method of claim 1, further comprising
   in response to the detecting operation, displaying a graphical user interface associated with the alarm condition.

8. A ventilation system including an alarm system adapted to provide respiratory therapy to a patient when the alarm system is in an alarm state, the ventilation system comprising:
   a first and second interactive indicator, the first and second interactive indicators visible in a 360 degree arc when viewed from a predetermined height;
   a processor communicably coupled to a computer readable medium, wherein the computer readable medium includes instructions executable by the processor to:
   generate an alarm indication associated with the alarm state via the first interactive indicator, wherein the alarm indication includes lighting the first interactive indicator;
   detect an operator's input at one of the first and second interactive indicators, wherein the operator's input is a direct interaction at one of the first and second interactive indicators;
   determine a type of input corresponding to the operator's input; and
   modify the alarm indication based on the determined type of input and the interactive indicator at which the operator's input was detected.

9. The ventilation system of claim 8, wherein the computer readable medium includes instructions executable by the processor to:
   modify the alarm indication by lowering the volume from an audible alarm.

10. The ventilation system of claim 8, wherein the computer readable medium includes instructions executable by the processor to:
    modify the alarm indication by ceasing emission of an audible alarm.

11. The ventilation system of claim 8, wherein the plurality of input types includes: a tap, and a touch starting from one side of the indicator and going to the other side to the other side of the indicator.

12. The ventilation system of claim 8, wherein each of the plurality of interactive indicators are comprised of at least one interactive element, wherein the interactive element is selected from one of: a push switch or touch-sensitive technology.

13. The ventilation system of claim 8, wherein the computer readable medium includes instructions executable by the processor to:
    modify the alarm indication by resetting the alarm system.

14. The ventilation system of claim 9, wherein the computer readable medium includes instructions executable by the processor to:
    in response to detection of an operator's input, display a graphical user interface on the ventilation system associated with the alarm condition.

15. An interactive alarm indication system for use on a ventilator comprising:
    one or more interactive indicators, each interactive indicator comprising an interactive element, the one or more indicators visible in a 360 degree arc around the interactive alarm indication system when viewed from a predetermined height, the one or more indicators including:
    a current status indicator adapted to display a different color or a different combination of color and behavior based on a current status of the ventilator;
    a secondary indicator adapted to display a different color or a different combination of color and behavior based on a highest historical status of the ventilator;
    wherein the current status indicator and the secondary indicator are further configured to:
    identify an alarm condition;
    generate an alarm indication associated with the alarm condition at the interactive indicator;
    detect an operator's input at the interactive element, wherein the operator's input is a direct interaction at one of the first and second interactive indicators;
    compare the operator's input to a plurality of input types;
    determine a type of input corresponding to the operator's input; and modify the alarm indication based on the determined type of input.

16. The interactive alarm indication system of claim 15, wherein the interactive element comprises a push switch.

17. The interactive alarm indication system of claim 15, wherein the indicator is comprised of a touch-sensitive technology including resistive, capacitive, or acoustic pulse recognition.

18. The interactive alarm indication system of claim 15, further comprising:
   a device configured to sound an audible alarm.

19. The interactive alarm indication system of claim 15, wherein the one or more indicators comprises multiple zones.

20. The interactive alarm indication system of claim 15, further comprising:
   an interactive exotic gas indicator adapted to indicate when an exotic gas is being delivered to a patient.

* * * * *